United States Patent [19]
Cude

[11] Patent Number: 5,527,299
[45] Date of Patent: Jun. 18, 1996

[54] ONE-PIECE ROTATOR AND MANIFOLD SYSTEM

[75] Inventor: J. Michael Cude, Woodburn, Ky.

[73] Assignee: Critical Disposables, Inc., Sanford, Fla.

[21] Appl. No.: 242,545

[22] Filed: May 13, 1994

[51] Int. Cl.$^6$ ............................................. A61M 25/00
[52] U.S. Cl. .......................... 604/280; 604/80; 604/905
[58] Field of Search ........................ 285/921; 604/9, 604/30, 32, 91, 246, 248, 249, 258, 284, 326, 82, 83, 86, 87, 88, 89, 90, 200, 201, 412, 413, 415, 416, 411, 905, 403, 80

[56] References Cited

U.S. PATENT DOCUMENTS

| | | |
|---|---|---|
| 457,503 | 8/1891 | Ball . |
| 738,503 | 9/1903 | Waters . |
| 883,941 | 4/1908 | Eagan . |
| 961,170 | 6/1910 | Shotwell . |
| 1,538,007 | 5/1925 | Schellin . |
| 2,414,997 | 1/1947 | Atkins . |
| 2,468,315 | 4/1949 | Wagner . |
| 2,476,172 | 7/1949 | Williams . |
| 2,532,669 | 12/1950 | Jones . |
| 2,542,701 | 2/1951 | Press . |
| 2,543,088 | 2/1951 | Woodling . |
| 2,560,263 | 7/1951 | Wiegand et al. . |
| 2,570,406 | 10/1951 | Troshkin et al. . |
| 2,574,625 | 11/1951 | Coss . |
| 2,655,391 | 10/1953 | Atkins . |
| 2,793,912 | 5/1957 | Krohm . |
| 2,893,395 | 7/1959 | Buck . |
| 2,963,304 | 12/1960 | Comlossy, Jr. et al. . |
| 3,392,993 | 7/1968 | Myers . |
| 3,484,121 | 12/1969 | Quinton . |
| 3,503,385 | 3/1970 | Stevens . |
| 3,785,683 | 1/1974 | Adelhed . |
| 3,799,589 | 3/1974 | Boelkins . |
| 3,876,234 | 4/1975 | Harms . |
| 3,922,011 | 11/1975 | Walters . |
| 3,957,293 | 5/1976 | Rodgers . |
| 4,152,017 | 5/1979 | Abramson . |
| 4,214,358 | 7/1980 | Clerc . |
| 4,216,982 | 8/1980 | Chow . |
| 4,254,773 | 3/1981 | Waldbillig . |
| 4,417,887 | 11/1983 | Koshi . |
| 4,580,816 | 4/1986 | Campbell et al. ....................... 285/921 |
| 4,629,455 | 12/1986 | Kanno ................................... 604/905 |
| 4,697,832 | 10/1987 | Dickirson . |
| 4,802,696 | 2/1989 | Chohon et al. ......................... 285/921 |
| 4,844,512 | 7/1989 | Gahwiler .............................. 285/921 |
| 5,104,156 | 4/1992 | Carlson . |
| 5,217,432 | 6/1993 | Rudzena et al. . |
| 5,263,945 | 11/1993 | Byrnes et al. . |
| 5,334,170 | 8/1994 | Moroski ................................. 604/80 |

FOREIGN PATENT DOCUMENTS

| | | |
|---|---|---|
| 493840 | 5/1954 | Italy . |
| 28289 | of 1912 | United Kingdom . |
| 1067286 | 5/1967 | United Kingdom . |

Primary Examiner—Corrine M. Maglione
Assistant Examiner—N. Kent Gring
Attorney, Agent, or Firm—Willian Brinks Hofer Gilson & Lione

[57] ABSTRACT

The invention provides a one-piece rotator and manifold system and method of operating the same. The system comprises a manifold having an integral stem formed on its proximal end, a O-ring, and a cylindrical outer member. The integral stem has a spigot and a circular flange having a stepped surface which are received in a recess formed in the cylindrical outer member. The O-ring is disposed within the recess and encircles the spigot. During pressurization, the stepped surface is forced axially and radially into the outer cylindrical member and acts to prevent the outer cylindrical member from decoupling from the manifold.

22 Claims, 3 Drawing Sheets

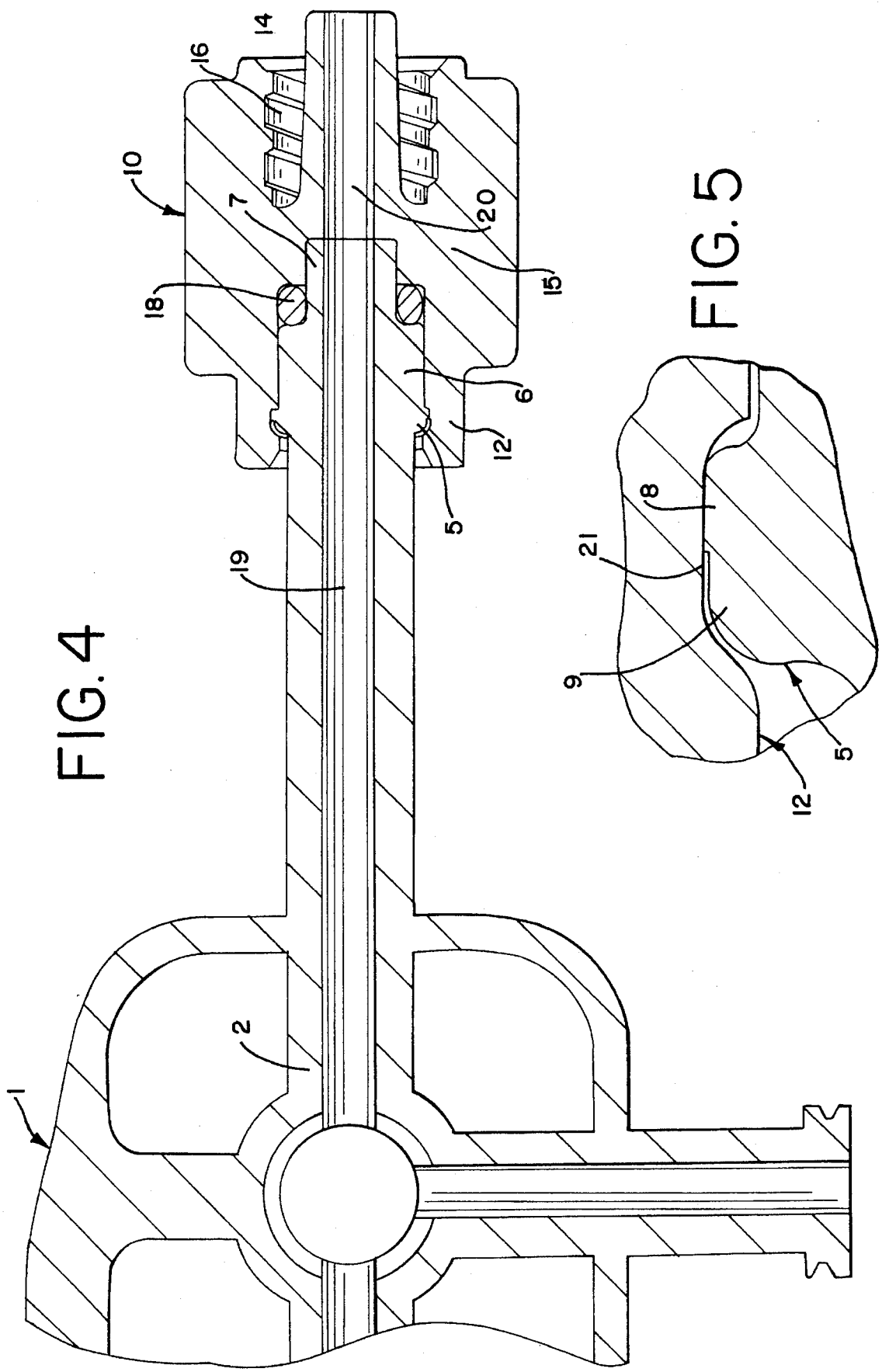

ONE-PIECE ROTATOR AND MANIFOLD SYSTEM

BACKGROUND OF THE INVENTION

This invention relates to a rotatable coupling system primarily used in heart catheterization, and method of operating the same.

Catheterization procedure requires that a catheter be first connected to a fluid pressure source and then threaded through a blood vessel in the patient's arm and into the heart. The catheter must remain connected to the source of fluid to avoid exposure of the antiseptic catheter to bacteria during the insertion process. The path from the blood vessel to the heart is tortuous and requires the catheter to rotate while remaining connected to the fluid source. To allow for this rotation, rotatable couplings or rotators are used.

High pressure injectors used in heart catheterization require the rotator to withstand fluid pressures in the 650–700 psi range without leaking or separating. Existing high pressure rotators are made with three pieces that are ultrasonically welded together and bonded to a manifold. FIG. 6 shows a cross section of a three piece rotator bonded to a manifold. The first outer piece 40 is ultrasonically welded at weld joint 44 to the second outer piece 41 to retain the inner piece 42 and O-ring 43. The first outer piece 40 has a standard male Luer 48 formed therein for locking with a female standard Luer member on the end of a catheter. One end of the inner piece 42 is bonded at bond joint 45 to the stem 46 of the manifold 47.

One problem with the three-piece rotator assembly is that it requires a bonding joint 45 to connect the assembly to the manifold. First, the bonding joint creates a visual obstruction. The bonding process leaves an approximately ¼ inch blind spot in the coupling which may prevent recognition of air bubbles formed in the fluid within the coupling. Second, the bonded connection may be a source of leaks. Third, the bonding process may create bonded bubbles which are actually bonded into the joint, but give the appearance of air bubbles in the fluid pathway. Fourth, the bonding process may leave a small bonding gap 49 between the rotator assembly and the manifold, which provides an area for air bubbles to be entrapped. Fifth, the bonding process requires the use of Methylene Chloride (Dichloromethane) which has been listed as a hazardous chemical by O.S.H.A.

A second problem with the three-piece rotator assembly is the requirement that the two outer pieces be ultrasonically welded. The weld joint may become a failure point during high pressure fluid flow.

A third problem with the three-piece rotator assembly is that the fluid path is composed of a series of varying diameters which allow areas for bubble entrapment and create turbulence in the fluid pathway.

A fourth problem with the three-piece rotator assembly is the significant labor required in the assembly operation. First, the three pieces or subassemblies must be manufactured. Next, the two outer subassemblies must be ultrasonically welded together and bonded to the manifold.

SUMMARY OF THE INVENTION

It would be desirable to have a rotator design that would eliminate the problems associated with the three-piece rotators. A one-piece rotator that could be snapped over an integral stem molded onto the manifold would eliminate the visual obstruction problems associated with the bonded assemblies. In addition, a bondless rotator would eliminate the other problems associated with bonded assemblies, including leaks at the bond joint, bubble entrapment at the bond gap, and the use of Dichloromethane.

A one-piece rotator design would also result in a significant labor reduction. Not only would the bonding process be eliminated, but there would be no need to ultrasonically weld any pieces together.

It would also be desirable to have a rotator design that would provide a continuous smooth fluid pathway which would eliminate the varying diameters associated with existing three-piece rotator assemblies. A smooth fluid pathway of a single diameter would eliminate bubble entrapment areas as well as reducing turbulence.

It would also be desirable to have the integral stem of the manifold formed with a stepped flange. During injection and high pressure fluid flow the sharp edge of the outer flange would cut into the surrounding one-piece rotator and prevent separation of the rotator from the stem.

The invention provides a rotatable coupling system and method of operating the same. The system comprises an integral stem formed on a proximal end of a manifold, and a rotator. The integral stem has a spigot and a circular flange. The rotator has a recess formed therein for receiving the spigot and for snap-fitting over the circular flange.

The invention further provides other features including: an O-ring being disposed within the recess and encircling the spigot, the circular flange having a first portion adjacent to the second portion, and having a larger diameter than the second portion; the rotator having a male standard Luer formed therein; the rotator having a cylindrical fluid pathway formed therein and axially aligned with and having the same diameter as a cylindrical fluid pathway formed in the manifold; the first portion of the flange having a sharp edge for cutting into the rotator during pressurized fluid flow; the O-ring further compressing both axially and radially during pressurized fluid flow; the rotator being a one piece polycarbonate member; and the first portion of the flange having a diameter of about 0.004 inches greater than said second portion.

The invention further provides for a rotatable coupling system comprising a manifold having a proximal stem, a cylindrical outer member, and an O-ring. A circular flange is formed integrally with and extends radially outward from the integral stem. A cylindrical portion is formed integrally with the stem and extends from the stem. The cylindrical portion has a smaller diameter than the stem. The cylindrical outer member has a recess formed therein for receiving the cylindrical portion of the stem and for snap-fitting over the circular flange. The O-ring is received in the recess and encircles the cylindrical portion.

The rotatable coupling system includes the following additional features: the flange having a first portion formed nearest the proximal end of the stem, and the flange having a second portion formed adjacent the first portion, the first portion having a greater diameter than said second portion; the first portion of the flange having a lip extending perpendicular to an outer surface of the second portion, and the lip having a sharp outer edge; the cylindrical outer member having a locking groove formed therein for retaining the circular flange; the recess having a first recess area for receiving the stem and cylindrical portion, and a second recess area for receiving the cylindrical portion, the stem having a cylindrical fluid pathway formed therein in communication with a cylindrical fluid pathway formed in the outer member, the fluid pathways having the same diameter; and the outer member and the manifold being formed of polycarbonate for allowing the sharp edge of the lip to cut into said outer member during pressurization.

The invention further provides for a method of operating the rotatable coupling system under high pressure fluid injection. Fluid is injected into a distal end of a central lumen of a manifold. Formed at a proximal end of the central lumen is a circular flange with a stepped outer surface radially extending from a cylindrical body of the central lumen, and a spigot axially extending from the cylindrical body. The spigot and flange are received in a recess formed in a rotator. The pressurized fluid is flowed through a fluid pathway formed in the central lumen, spigot and rotator. The stepped outer surface of the flange is radially and axially forced into the outer body to prevent it from separating from the manifold during injection.

The method further provides additional features including: an O-ring encircling the spigot, and the O-ring being compressed both axially and radially within the recess to form a fluid tight seal; further axially compressing the O-ring as the system is pressurized; the circular flange comprising a first portion and a second portion forming the stepped surface, the first portion having a greater diameter than the second portion, the first portion having a lip extending perpendicular from the outer surface of the second portion, the lip having a sharp outer edge for cutting into an inner surface of a collar portion of the rotator for preventing the rotator body from separating from the manifold; the rotator having a male standard Luer taper formed therein and projecting coaxially through and beyond the cylindrical body for allowing a catheter to be attached thereto.

The present invention, together with its attendant objectives and advantages, will be further understood with reference to the detailed description and the accompanying drawings.

BRIEF DESCRIPTION OF THE DRAWINGS

FIG. 4 is a cross sectional view of the integral one-piece rotator system.

FIG. 5 is an enlarged cross sectional view of the stepped flange and collar.

DETAILED DESCRIPTION OF AN EMBODIMENT

Figure 1:
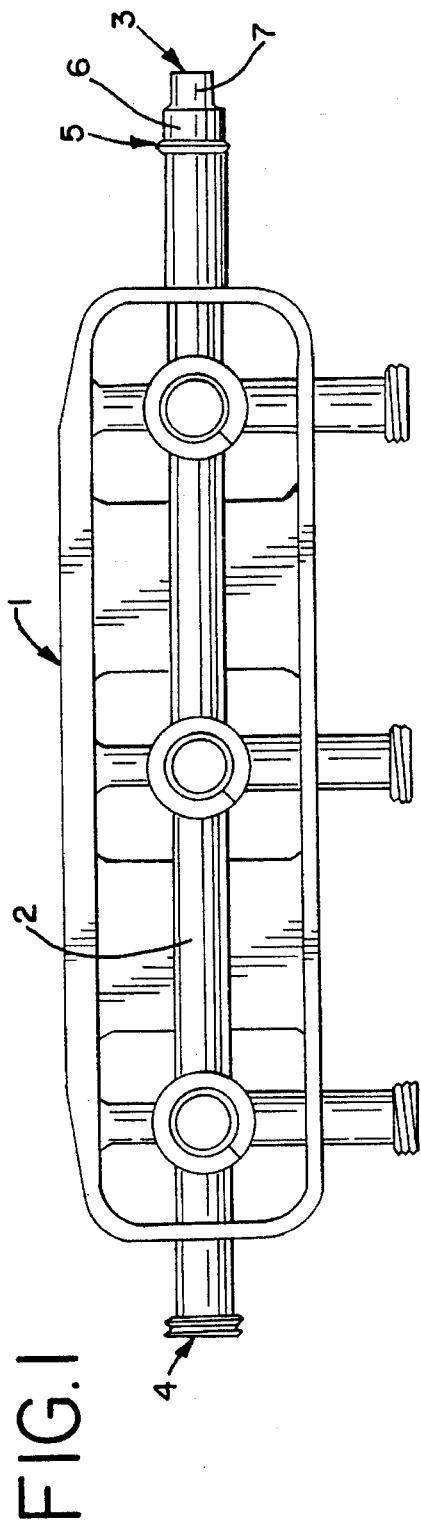
FIG. 1 is a side elevational view of the manifold having the integral molded stem.

Referring to FIG. 1, a side elevational view of the manifold is shown. The manifold 1 has central lumen 2 having a proximal end 3 and a distal end 4. The proximal end has formed thereon an integral stem having a circular flange 5 extending radially from the cylindrical body portion 6, and a spigot 7 extending axially from the cylindrical body portion 6.

Figure 2:
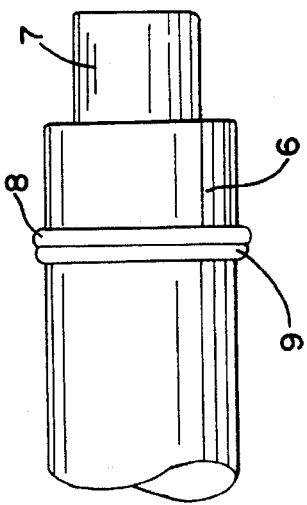
FIG. 2 is an enlarged side elevational view of the integral stem.

Referring to FIG. 2, the circular flange 5 has a stepped surface formed by a first portion 8 having a diameter of 0.2860±0.0005 inches, which is slightly greater than the second portion 9 which has a diameter of 0.2820±0.0005 inches.

Figure 3:
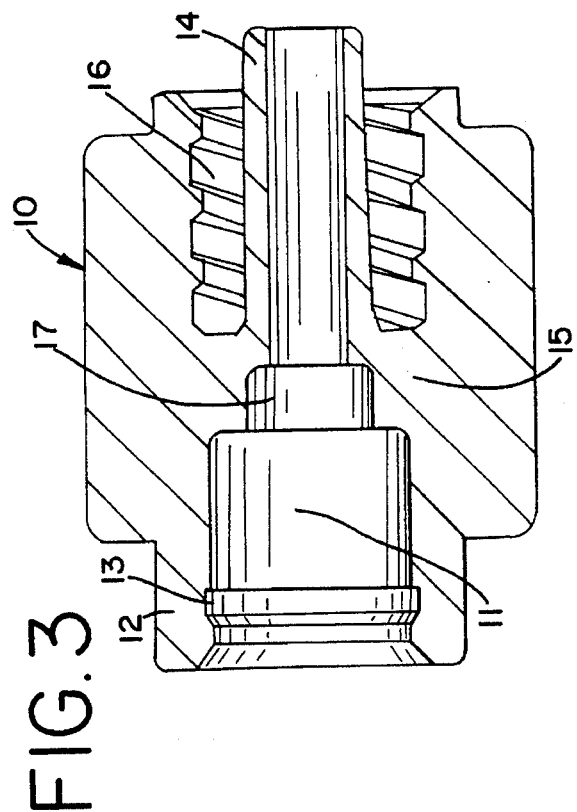
FIG. 3 is an enlarged cross sectional view of the one-piece snap-on rotator.
Figure 6:
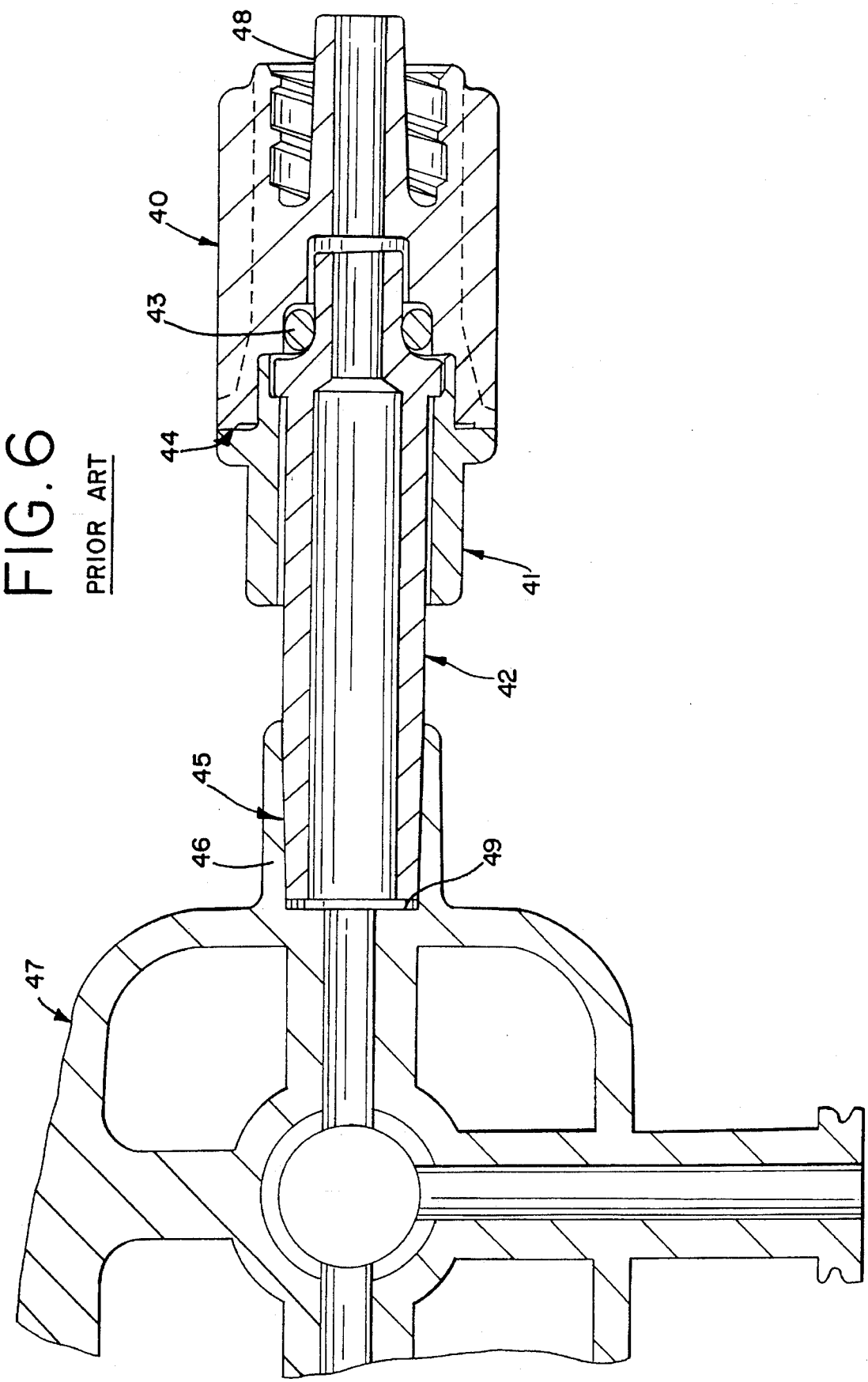
FIG. 6 is a cross sectional view of a three-piece rotator system.

Referring to FIG. 3 a cross sectional view of the one-piece rotator 10 is shown. The rotator 10 has a central body portion 15, and a collar portion 12. Formed in the central body and collar portion is a first recess 11 for receiving the cylindrical body portion and spigot of the integral stem. A second recess 17 has a smaller diameter for receiving and axially aligning the spigot 7. The collar portion 12 snaps over the circular flange 5, and the flange is received within the locking groove 13. Projecting coaxially through and beyond the central body is a male standard Luer taper 14. The internal surface of the central body has a standard Luer thread 16 providing a Luer lock connector.

Referring to FIG. 4, a cross sectional view of the integral one-piece coupling is shown. An O-ring 18 is located in the first recess area 11 of the one-piece rotator and encircles the spigot 7. The fluid pathway 19 formed in the central lumen and integral stem of the manifold is axially aligned and has the same diameter as the fluid pathway 20 formed in the central body and male Luer of the one-piece rotator.

Referring to FIG. 5, an enlarged cross sectional view of the collar portion 12 and circular flange 5 is shown. The first portion 8 of the circular flange has a lip 21 extending perpendicular to the outer surface of the second portion 9. The lip 21 has a sharp outer edge that can cut into the collar portion 12 when the integral coupling is pressurized.

In operation, one end of a catheter, having a female Luer is locked with the male Luer 14 formed in the one-piece rotator 10. The distal end 4 of the manifold is connected to a high pressure injector. The MEDRAD™ injector, which is commonly used for heart catheterization, is normally operated at pressures of between 650–700 psi for the catheterization procedure.

The catheter is then inserted through blood vessel in the patients arm and forced through the tortuous path into the patients heart. The one-piece rotator 10 is freely rotatable upon the integral stem during the threading process. Prior to injection, the O-ring 18 is compressed both axially and radially between two sets of surfaces forming a fluid tight seal. In the axial direction, the O-ring is compressed against an outer shoulder portion of the cylindrical body portion 6 of the integral stem and the inner wall of the central body 15 of the rotator. In the radial direction, the O-ring is compressed against the outer wall of the spigot 7 and the inner wall of the central body 15 of the rotator. Once the catheter is in place, there is no need to disconnect the catheter, which is already connected to the injector and fluid source.

Next, the fluid (contrast medium) is injected under high pressure through the distal end 4 of the manifold by the high pressure injector. The injected contrast medium flows through the central lumen 2 to the proximal end 3. The high pressure causes the O-ring 18 to further compress both axially and radially and the fluid tight seal is maintained between the two sets of surfaces. The high pressure also causes the sharp outer edge of the lip 21 of the flange 5 to be axially and radially forced into the inner wall of the collar 12. Both the one-piece rotator and the integral stem are composed of polycarbonate, which allows the sharp edge of the lip 21 to cut into the collar 12 and prevents the collar from riding up over the flange 5 and separating from the manifold.

While the invention has been described in reference to a certain embodiment, those skilled in the art will recognize modification of structure, arrangement, composition and the like that can be made to the present invention that will fall within the scope of the invention claimed.

I claim:

1. A rotatable coupling system comprising:
   a manifold having an integral stem formed on a proximal end of said manifold, said integral stem having a spigot and a circular flange; and
   a rotator having a recess formed therein for receiving the spigot and for snap-fitting over the circular flange.

2. The rotatable coupling system of claim 1 further comprising an O-ring disposed within said recess and encircling said spigot.

3. The rotatable coupling system of claim 2 wherein the O-ring being compressed both axially and radially.

4. The rotatable coupling system of claim 1 wherein said circular flange having a first and second portion, said first portion adjacent to said second portion and having a larger diameter than said second portion.

5. The rotatable coupling system of claim 4 wherein said first portion having a sharp edge for cutting into the rotator during pressurized fluid flow.

6. The rotatable coupling system of claim 4 wherein the first portion of said flange having a diameter of about 0.004 inches greater than said second portion.

7. The rotatable coupling system of claim 1 wherein said rotator having a male standard Luer formed on an end of the rotator opposite said recess, and said male standard Luer having a fluid pathway in communication with said recess.

8. The rotatable coupling system of claim 1 wherein said rotator having a cylindrical fluid pathway formed therein axially aligned and having the same diameter as a cylindrical fluid pathway formed in said manifold.

9. The rotatable coupling system of claim 1 wherein the rotator is a one piece polycarbonate member.

10. The rotatable coupling system of claim 1 further comprising a fluid pathway formed through said integral stem and said rotator, said system comprising a clear material for providing a view of the fluid pathway that is free from visual obstruction.

11. A rotatable coupling system comprising:
    a manifold having a proximal stem;
    a circular flange formed integrally with and extending radially outward from said stem,
    a cylindrical portion formed integrally with said stem and axially extending from said stem, said cylindrical portion having a smaller diameter than said stem;
    a cylindrical outer member having a recess formed therein for receiving the cylindrical portion of the stem and for snap-fitting over the circular flange; and
    an O-ring received in said recess and encircling said cylindrical portion.

12. The rotatable coupling system of claim 11 wherein the flange having a first portion formed nearest the proximal end of the stem, and said flange having a second portion formed adjacent said first portion, said first portion having a greater diameter than said second portion.

13. The rotatable coupling system of claim 12 wherein the first portion of the flange having a lip extending perpendicular to an outer surface of the second portion, said lip having a sharp outer edge.

14. The rotatable coupling system of claim 13 wherein said outer member and said manifold are formed of polycarbonate for allowing said sharp edge of said lip to cut into said outer member during pressurization.

15. The rotatable coupling system of claim 11 wherein the cylindrical outer member having a locking groove formed therein for retaining the circular flange.

16. The rotatable coupling system of claim 11 wherein the recess having a first recess area for receiving the stem and spigot, and a second recess area for receiving the spigot, said stem having a cylindrical fluid pathway formed therein in communication with a cylindrical fluid pathway formed in said outer member, said fluid pathways having the same diameter.

17. The system of claim 16 wherein the system comprises a clear material for providing a view of the fluid pathways that is free from visual obstruction.

18. A method of operating a rotatable coupling system under high pressure fluid injection comprising:
    injecting fluid into a distal end of a central lumen of a manifold, said central lumen having formed at a proximal end a circular flange with a stepped outer surface extending radially from a cylindrical body of the central lumen, and a spigot axially extending from the cylindrical body, said spigot and flange being received in a recess formed in a rotator,
    flowing the pressurized fluid through a fluid pathway formed in the central lumen, spigot and rotator; and
    forcing the stepped surface of the flange radially and axially into the collar portion to prevent the outer body from separating from the manifold during injection.

19. The method of claim 18 further comprising an O-ring encircling the spigot, said O-ring being compressed both axially and radially within the recess to form a fluid tight seal.

20. The method of claim 19 further comprising further axially compressing the O-ring as the system is pressurized.

21. The method of claim 18 wherein the circular flange comprises a first portion and a second portion forming the stepped surface, said first portion having a greater diameter than the second portion, said first portion having a lip extending perpendicular from the outer surface of the second portion, said lip having a sharp outer edge for cutting into an inner surface of a collar portion of the rotator for preventing the rotator body from separating from the manifold.

22. The method of claim 18 wherein the rotator has a male standard Luer taper formed therein and projecting coaxially through and beyond the cylindrical body for allowing a catheter to be attached thereto.

* * * * *

UNITED STATES PATENT AND TRADEMARK OFFICE
CERTIFICATE OF CORRECTION

PATENT NO. : 5,527,299
DATED : June 18, 1996
INVENTOR(S) : J. Michael Cude

It is certified that error appears in the above-indentified patent and that said Letters Patent is hereby corrected as shown below:

<u>On the Title Page</u>

Under the heading "References Cited FOREIGN PATENT DOCUMENTS", line 2, delete "of 1912" and substitute --12/1912--.

Signed and Sealed this

Twenty-eighth Day of October, 1997

Attest:

BRUCE LEHMAN

Attesting Officer

Commissioner of Patents and Trademarks